United States Patent [19]

Fried

[11] Patent Number: 4,761,488
[45] Date of Patent: Aug. 2, 1988

[54] REACTION OF OLEFINS WITH MALEIC ANHYDRIDE

[75] Inventor: Herbert E. Fried, Houston, Tex.

[73] Assignee: Shell Oil Company, Houston, Tex.

[21] Appl. No.: 120,257

[22] Filed: Nov. 13, 1987

[51] Int. Cl.⁴ ............................................. C07D 307/60
[52] U.S. Cl. ..................................................... 549/255
[58] Field of Search ........................................ 549/255

[56] References Cited

U.S. PATENT DOCUMENTS

| | | | |
|---|---|---|---|
| 4,257,958 | 3/1981 | Powell | 260/346.7 |
| 4,278,604 | 7/1981 | Powell | 260/346.7 |
| 4,396,774 | 8/1983 | Schaffhausen | 549/255 |
| 4,599,433 | 3/1986 | Bronstert et al. | 549/255 |
| 4,599,433 | 7/1986 | Bronstert et al. | 549/255 |

FOREIGN PATENT DOCUMENTS 57-035581  2/1982  Japan .................................. 549/255

*Primary Examiner*—Mary Lee
*Assistant Examiner*—Bernard I. Dentz
*Attorney, Agent, or Firm*—Pamela J. McCollough

[57] ABSTRACT

Olefinically unsaturated hydrocarbons are reacted with maleic anhydride to form the corresponding succinic anhydride, in the presence of an additive, aluminum acetylacetonate, which prevents side reactions. These products are used for the preparation of anticorrosive agents.

3 Claims, No Drawings

REACTION OF OLEFINS WITH MALEIC ANHYDRIDE

FIELD OF THE INVENTION

This invention relates to a process in which olefinically unsaturated hydrocarbons are reacted with maleic anhydride to form the corresponding alkenyl succinic anhydride, in the presence of an additive which prevents side-reactions.

BACKGROUND OF THE INVENTION

Reactions of olefins with maleic anhydride at elevated temperatures give the corresponding adducts in accordance with the following equation:

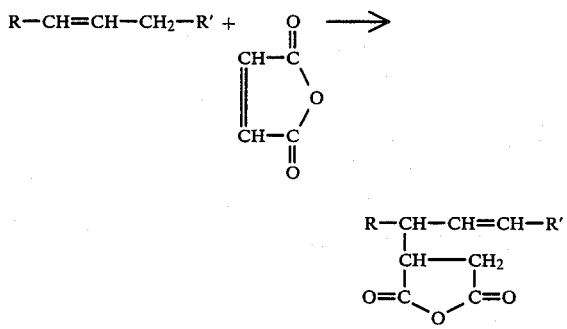

However, reactions of this type require very long reaction times even at elevated temperatures. In addition, under conventional temperature conditions (200°–300° C.), darkening of the product and formation of black solids are typically observed. These problems are believed to arise from secondary reactions involving maleic anhydride such as, for example, polymerization and decarboxylation. Thus, stabilization of maleic anhydride for these secondary reactions and acceleration of the addition reaction is desirable.

It is known that the reaction of the olefinically unsaturated hydrocarbons with maleic anhydride can be carried out in the presence of a catalytically effective amount of an additive in order to accelerate the reaction. For example, in conventional processes, the reaction times are reduced to a satisfactory level by carrying out the addition reactions in the presence of small amounts, in general from 1 to 5000 ppm by weight, of substances such as furan derivatives (U.S. Pat. No. 4,388,471), iodine (Great Britain Patent Application No. 356,882), bromine (Great Britain Patent Application No. 1,480,453), an α-bromodialkylketone (U.S. Pat. No. 3,953,475 and U.S. Pat. No. 3,954,812), hydrogen chloride or calcium bromide (U.S. Pat. No. 3,935,249), a hydantoin derivative (U.S. Pat. No. 3,927,041), p-toluenesulfonic acid (U.S. Pat. No. 3,855,251), a nickel salt (Great Britain Patent Application No. 2,081,274) or a bromophenol (U.S. Pat. No. 4,278,604).

A process for thermally stabilizing acid anhydrides by the addition of an inorganic boron-oxygen compound is taught in U.S. Pat. No. 4,257,958, the teachings of which are herein incorporated by reference.

U.S. Pat. No. 4,599,433, the teachings of which are herein incorporated by reference, is directed to a process for the reaction of an olefinically unsaturated hydrocarbon with maleic anhydride in which an alkoxide of titanium, zirconium, vandium or aluminum is used as the additive.

In these conventional processes, however, the degree of conversion of the olefin is frequently low. In addition, where halogen compounds are used, there is also considerable danger due to the toxicity of the resulting reaction mixture. Many of these conventional processes also have the disadvantages of product discoloration and formation of solids during the reaction which contaminate the kettle walls or, in more adverse cases, the reaction product. An even more disadvantageous feature is the formation of resin-like residues which render the product useless if it cannot be purified by distillation or filtration.

It has now been found that small amounts of aluminum acetylacetonate as additive dramatically reduce the formation of black solids and improve product color for the reaction of maleic anhydride and olefinically unsaturated hydrocarbons to produce alkenyl succinic anhydrides. The presence of this additive permits the reaction to be conducted at higher temperatures which decreases residence times and allows complete consumption of maleic anhydride to avoid plugging or recycle.

SUMMARY OF THE INVENTION

This invention relates to a process for the reaction of an olefinically unsaturated hydrocarbon, which has a molecular weight in the range of from about 100 to about 3000, with maleic anhydride in a molar ratio of maleic anhydride to olefin of from about 0.4 to about 5:1, in the presence of from 1 to about 5000 ppm by weight, based on the olefin, of an additive which reduces side reactions, at from about 160° C. to about 260° C., with formation of the corresponding succinic anhydride wherein the additive used is aluminum acetylacetonate.

It is an object of this invention to provide a process for the addition reaction of olefins with maleic anhydride in which the formation of resin by the maleic anhydride is reduced and the color of the reaction product is improved.

DESCRIPTION OF THE PREFERRED EMBODIMENTS

The present invention relates to a process for the reaction of an olefinically unsaturated hydrocarbon with maleic anhydride to form the corresponding succinic anhydride in the presence of an additive which reduces side reactions.

Suitable olefinically unsaturated hydrocarbons for the instant invention are all compounds which possess terminal double bonds or double bonds within a chain and have a molecular weight in the range of from about 100 to about 3000, and mixtures of these compounds.

The term "olefinically unsaturated hydrocarbons" as used herein, refers to monomeric, oligomeric and polymeric $C_2$–$C_{25}$ alkenes whose chains may or may not be branched and which have a molecular weight in the range of from about 100 to about 3000. The olefinic unsaturated hydrocarbons which can be subjected to the addition reaction include, for example, tetradecene-1, oct-1-ene, 2,4,4-trimethylpent-2-ene, 2-methyl-5-propylhex-1-ene, 3-cyclohexyl-bute-1-ene and the oligomers of $C_2$–$C_{20}$ olefins, for example the oligomers of ethylene, propylene, bute-1-ene, isobutene, hex-1-ene, oct-1-ene, and the like, and the polyisobutenes where the molecular weight is from about 350 to about 3000, and diisobutene. Preferred olefinically unsaturated hydrocarbons are $C_{15}$–$C_{20}$ linear or branched internal olefins and alpha olefins.

In the reaction of the olefinically unsaturated hydrocarbons with maleic anhydride, the molar ratio of maleic anhydride to olefin, i.e., the proportions of substances based on the number of moles of components, is typically from about 0.4:1 to about 5.0:1, preferably from about 0.65:1 to about 1.2:1, more preferably from about 0.8:1 to about 1:1. A process in which equal molar amounts of olefin and maleic anhydride can be used is particularly preferred.

To avoid side reactions during the addition reaction of maleic anhydride, the reaction is carried out in the presence of from 1 to about 5000, preferably from about 5 to about 1000, ppm by weight, based on the weight of the reactants used, of an additive which is intended to accelerate the desired addition reaction. The principle side reactions are believed to be the formation of poly(maleic anhydride), which is obtained as a solid residue, or poly(maleic anhydride) with an olefinic component from free radical copolymerization of the olefin and the maleic anhydride. The addition reaction with formation of the corresponding succinic anhydrides takes place at from about 160° C. to about 260° C., preferably from about 230° C. to about 245° C. The reaction is preferably carried out in an agitated reactor in the presence or absence of a solvent, although no solvent is typically required. The reaction times are typically from about 1 hour to about 20 hours, preferably from about 4 hours to about 10 hours more preferably from about 3.5 hours to about 7 hours, and most preferably from about 3.5 hours to about 5 hours. In a preferred embodiment, the reaction is carried out in an essentially oxygen-free atmosphere in the presence of an inert gas. A nitrogen or argon atmosphere is preferably used as the inert atmosphere. When the reaction is complete, the autoclave is left to cool and the reaction mass is preferably worked up by distillation. As far as possible, the reactants should be anhydrous.

In the novel process, the additive used is aluminum acetylacetonate. The aluminum acetylacetonate is in the solid state and is used in this form in the additional reaction. One advantage obtained when the invention is used in the absence of solvents is the fact that no toxic halogen-containing products are formed. In addition, the use of small amounts of aluminum acetylacetonate dramatically reduce sludge-make and improve the product color for the reaction of maleic anhydrides and olefins to produce alkenyl succinic anhydrides.

The resulting maleic anhydride/olefin products having molecular weights in the range of from about 200 to about 350 are used for the preparation of anticorrosive agents for aqueous or organic systems. The resulting olefinic-succinic anhydrides having molecular weights in the range of from about 250 to about 3000 can be converted in simple manner to compounds which are suitable as oil additives such as for example, lubricant additives.

The instant invention will now be described by the use of the following examples which are intended to be illustrative and are not to be construed as limiting the scope of the invention.

EXAMPLE 1 37.0 Grams of tetradecene-1 having a molecular weight of 196 and 18.0 grams of maleic anhydride (a maleic anhydride to olefin ratio of 1:1) were reacted in a Fischer-Porter bottle in the presence of 0.01 grams of aluminum acetylacetonate while being stirred with a magnetic stirrer. The reaction mixture was then heated to 245° C. for 4 hours. The results of the experiment are presented in Table I.

EXAMPLE 2

The procedure of Example 1 was repeated except that 0.2 grams of aluminum acetylacetonate was used as additive. The results of the experiment are presentd in Table I.

EXAMPLE 3

37.0 Grams of $C_{15}$–$C_{20}$ internal olefins having a molecular weight of 239 was sparged with nitrogen for about 16 hours and then reacted with 12.1 grams of maleic anhydride (a maleic anhydride to olefin ratio of 0.8:1) in a Fischer-Porter bottle in the presence of 0.02 grams of aluminum acetylacetonate while being stirred with a magnetic stirrer. The reaction mixture was then heated to 230° C. for 20 hours. The results of the experiment are presented in Table II.

EXAMPLE 4

37.0 Grams of $C_{15}$–$C_{20}$ internal olefins having a molecular weight of 239 was sparged with nitrogen for about 16 hours and reacted with 12.1 grams of maleic anhydride (a maleic anhydride to olefin ratio of 0.8:1) in a Fischer-Porter bottle in the presence of 0.01 grams of aluminum acetylacetonate while being stirred with a magnetic stirrer. The reaction mixture was then heated to 245° C. for 20 hours. The results of the experiment are presented in Table II.

COMPARATIVE EXAMPLE A

The procedure of Example 1 was repeated except that no additive was used. The results of the experiment are presented in Table I.

COMPARATIVE EXAMPLE B

The procedure of Example 3 was repeated except that no additive was used. The results of the experiment are presented in Table II.

COMPARATIVE EXAMPLE C

The procedure of Example 4 was repeated except that no additive was used. The results of the experiment are presented in Table II.

As can be seen from Tables I and II, the presence of aluminum acetylacetonate as an additive in the reaction of olefins and maleic anhydride results in a product having reduced formation of side reactions of soluble and/or insoluble contaminants. In many cases, the use of this additive results in reduction of soluble by-products and improved product color. In other cases, for instance, for that shown in Comparative Example B, the invention results in reduced formation of insoluble by-products. Table II shows that the Klett color number of Comparative Example B is lower than that for Example 3. However, Comparative Example B, in which no additive was used, results in a product which contains substantial amounts of black solids and is, therefore, undesirable.

TABLE I

|  | Additive | Reaction Time Hrs. | Reaction Temperature, °C. | % Wt.[a] Alpha Olefin | % Wt.[a] Alkenylsuccinic Anhydride | Klett[b] Color |
|---|---|---|---|---|---|---|
| Example 1 | Aluminum acetylacetonate | 4 | 245 | 28.7 | 71.3 | 136 |
| Example 2 | Aluminum acetylacetonate | 4 | 245 | 24.4 | 75.6 | 295 |
| Comparative Example A | None | 4 | 245 | 26.5 | 73.4 | 560[c] |

[a]Determined by gas liquid chromatography. Wt. % alkenylsuccinic anhydride also includes the 2:1 maleic anhydride/olefin adduct (typically <6%).
[b]Shell method series 512/71.
[c]Significant amounts of black solids were observed in this product.

II

|  | Additive | Reaction Time Hrs. | Reaction Temperature, °C. | % Wt.[a] Internal Olefin | % Wt.[a] Alkenylsuccinic Anhydride | Klett[b] Color |
|---|---|---|---|---|---|---|
| Example 3 | Aluminum acetylacetonate | 20 | 230 | 25.7 | 74.3 | 330 |
| Comparative Example B | None | 20 | 230 | 38.0 | 62.0 | 286[c] |
| Example 4 | Aluminum acetylacetonate | 20 | 245 | 36.1 | 63.9 | 230 |
| Comparative Example C | None | 20 | 245 | 36.2 | 63.8 | 700[c] |

[a]Determined by gas liquid chromatography. Wt. % alkenylsuccinic anhydride also includes the 2:1 maleic anhydride/olefin adduct (typically <6%).
[b]Shell method series 512/71.
[c]Significant amounts of black solids were observed in this product.

We claim as our invention:

1. In a process for the reaction of olefinically unsaturated hydrocarbons with maleic anhydride to form the corresponding alkenyl succinic anhydride in the presence of an additive which reduces the formation of black/solids and improves product color, the improvement which comprises utilizing aluminum acetylacetonate as additive.

2. The improvement of claim 1 wherein an amount of aluminum acetylacetonate ranging from 1 ppm to about 5000 ppm by weight, based on total weight of olefinically unsaturated hydrocarbon and maleic anhydride, is used.

3. The improvement of claim 2 wherein an amount of aluminum acetylacetonate ranging from about 5 ppm to about 1000 ppm is used.

* * * * *